United States Patent
James

(10) Patent No.: US 12,214,114 B2
(45) Date of Patent: Feb. 4, 2025

(54) FLOW SYNCHRONIZATION DEVICES, METHODS, AND SYSTEMS

(71) Applicant: NxStage Medical, Inc., Lawrence, MA (US)

(72) Inventor: Jerome James, Vestavia, AL (US)

(73) Assignee: NxStage Medical, Inc., Lawrence, MA (US)

(*) Notice: Subject to any disclaimer, the term of this patent is extended or adjusted under 35 U.S.C. 154(b) by 503 days.

(21) Appl. No.: 17/612,905

(22) PCT Filed: May 22, 2020

(86) PCT No.: PCT/US2020/034420
§ 371 (c)(1),
(2) Date: Nov. 19, 2021

(87) PCT Pub. No.: WO2020/237228
PCT Pub. Date: Nov. 26, 2020

(65) Prior Publication Data
US 2022/0362448 A1    Nov. 17, 2022

Related U.S. Application Data

(60) Provisional application No. 62/851,922, filed on May 23, 2019.

(51) Int. Cl.
*A61M 1/34* (2006.01)
*A61M 1/16* (2006.01)

(52) U.S. Cl.
CPC .......... *A61M 1/341* (2014.02); *A61M 1/1603* (2014.02); *A61M 1/3441* (2013.01); *A61M 2205/3334* (2013.01)

(58) Field of Classification Search
CPC .. A61M 1/341; A61M 1/1603; A61M 1/3441; A61M 2205/3334
(Continued)

(56) References Cited

U.S. PATENT DOCUMENTS 4,009,078 A    2/1977 Wilkins et al.
4,728,433 A    3/1988 Buck et al.
(Continued)

FOREIGN PATENT DOCUMENTS

CN    103957957 A  *  7/2014  ......... A61B 5/02035
EP    2163271 B1      3/2010
(Continued)

OTHER PUBLICATIONS

Machine-generated English translation of CN 103957957, generated on Mar. 28, 2024.*

(Continued)

*Primary Examiner* — Fred Prince
(74) *Attorney, Agent, or Firm* — Potomac Law Group, PLLC

(57) ABSTRACT

A parameter for controlling an inlet pump speed in a hemofiltration system is derived from fitting a line to multiple data points of pressure versus pump speed. The pressure is measured in a channel connecting an inlet pump to an outlet pump. First, the inlet pump operates and the pressure is sampled until it is stabilized, then the inlet pump speed is increased and pressure is measured to obtain a data point. Subsequently the inlet pump speed is decreased and pressure is measured to obtain another data point. A line is fit through the data points to obtain the parameter.

7 Claims, 7 Drawing Sheets

(58) Field of Classification Search
USPC .................................. 210/646, 647, 737
See application file for complete search history.

(56) References Cited

U.S. PATENT DOCUMENTS

| | | | |
|---|---|---|---|
| 4,769,001 | A | 9/1988 | Prince |
| 4,894,150 | A | 1/1990 | Schurek et al. |
| 5,344,568 | A | 9/1994 | Kitaevich et al. |
| 5,792,367 | A | 8/1998 | Mattisson et al. |
| 5,836,908 | A | 11/1998 | Beden et al. |
| 5,932,103 | A | 8/1999 | Kenley et al. |
| 5,984,893 | A | 11/1999 | Ward |
| 6,217,539 | B1 | 4/2001 | Goldau |
| 6,221,672 | B1 | 4/2001 | Baugh et al. |
| 6,284,131 | B1 | 9/2001 | Hogard et al. |
| 7,112,273 | B2 | 9/2006 | Weigel et al. |
| 7,341,568 | B2 | 3/2008 | Zhang |
| 7,699,992 | B2 | 4/2010 | Sternby |
| 7,727,222 | B2 | 6/2010 | Silva et al. |
| 7,931,610 | B2 | 4/2011 | Murakami et al. |
| 8,012,114 | B2 | 9/2011 | Daniel et al. |
| 8,060,190 | B2 | 11/2011 | Sörnmo et al. |
| 8,086,323 | B2 | 12/2011 | Reghabi et al. |
| 8,092,414 | B2 | 1/2012 | Schnell et al. |
| 8,182,692 | B2 | 5/2012 | Gotch |
| 8,209,033 | B2 | 6/2012 | Zhang et al. |
| 8,216,478 | B2 | 7/2012 | Noack et al. |
| 8,239,010 | B2 | 8/2012 | Banet et al. |
| 8,246,546 | B2 | 8/2012 | Huiku |
| 8,246,567 | B2 | 8/2012 | Bene |
| 8,287,739 | B2 | 10/2012 | Barrett et al. |
| 8,361,006 | B2 | 1/2013 | Kraemer |
| 8,524,154 | B2 | 9/2013 | Shekalim et al. |
| 8,529,767 | B2 | 9/2013 | Zhang |
| 8,583,226 | B2 | 11/2013 | Moissl et al. |
| 8,591,865 | B2 | 11/2013 | Wang et al. |
| 8,613,705 | B2 | 12/2013 | Scheurer et al. |
| 8,632,485 | B2 | 1/2014 | Schlaeper et al. |
| 8,663,931 | B2 | 3/2014 | Saito et al. |
| 8,792,089 | B2 | 7/2014 | Zhang et al. |
| 8,858,486 | B2 | 10/2014 | Zhang et al. |
| 8,900,172 | B2 | 12/2014 | Pohlmeier |
| 9,037,207 | B2 | 5/2015 | Al-Ali et al. |
| 9,144,639 | B2 | 9/2015 | Vantard et al. |
| 9,220,827 | B2 | 12/2015 | Meibaum et al. |
| 9,278,171 | B2 | 3/2016 | Brandl et al. |
| 9,381,289 | B2 | 7/2016 | Hedmann et al. |
| 9,423,338 | B2 | 8/2016 | Alic et al. |
| 9,566,377 | B2 | 2/2017 | Jones et al. |
| 9,610,393 | B2 | 4/2017 | Rada et al. |
| 9,724,455 | B2 | 8/2017 | Kopperschmidt et al. |
| 9,743,843 | B2 | 8/2017 | Chamney et al. |
| 9,795,739 | B2 | 10/2017 | Al-Ali et al. |
| 9,814,412 | B2 | 11/2017 | Zhang et al. |
| 9,943,633 | B2 | 4/2018 | Sigg et al. |
| 9,968,298 | B2 | 5/2018 | Heppe et al. |
| 9,980,663 | B2 | 5/2018 | Wabel et al. |
| 9,987,406 | B2 | 6/2018 | Wright et al. |
| 10,001,454 | B2 | 6/2018 | Schick et al. |
| 10,010,289 | B2 | 7/2018 | Gagel et al. |
| 10,016,549 | B2 | 7/2018 | Stonger et al. |
| 10,092,249 | B2 | 10/2018 | Kiani et al. |
| 10,098,993 | B2* | 10/2018 | Meyer ................ A61M 1/1696 |
| 10,117,590 | B2 | 11/2018 | Barrett et al. |
| 10,155,077 | B2 | 12/2018 | Maierhofer et al. |
| 10,328,192 | B2 | 6/2019 | Jansson et al. |
| 2001/0016699 | A1 | 8/2001 | Burbank et al. |
| 2003/0113933 | A1 | 6/2003 | Jansson et al. |
| 2004/0245161 | A1 | 12/2004 | Treu et al. |
| 2005/0113735 | A1 | 5/2005 | Brugger et al. |
| 2005/0113757 | A1 | 5/2005 | McFarlane |
| 2005/0126961 | A1 | 6/2005 | Bissler et al. |
| 2005/0133735 | A1 | 6/2005 | Tatsumi et al. |
| 2005/0251086 | A1 | 11/2005 | Sternby |
| 2009/0076434 | A1 | 3/2009 | Mischelevich et al. |
| 2009/0078622 | A1 | 3/2009 | Zhang et al. |
| 2010/0016777 | A1 | 1/2010 | Burbank et al. |
| 2010/0099958 | A1 | 4/2010 | Kotanko et al. |
| 2010/0112583 | A1 | 5/2010 | Ichiishi et al. |
| 2010/0137693 | A1 | 6/2010 | Porras et al. |
| 2010/0192686 | A1* | 8/2010 | Kamen ................ A61M 1/3672 715/764 |
| 2010/0247377 | A1 | 9/2010 | Tsutsumida et al. |
| 2010/0298751 | A1 | 11/2010 | Schulte et al. |
| 2011/0000830 | A1 | 1/2011 | Ikeda |
| 2011/0066043 | A1 | 3/2011 | Banet et al. |
| 2011/0077474 | A1 | 3/2011 | Huiku |
| 2011/0132838 | A1 | 6/2011 | Curtis et al. |
| 2011/0208072 | A1 | 8/2011 | Pfeiffer et al. |
| 2011/0230744 | A1 | 9/2011 | Ripoll et al. |
| 2012/0118801 | A1 | 5/2012 | Rada et al. |
| 2012/0150049 | A1 | 6/2012 | Zielinski et al. |
| 2012/0181189 | A1 | 7/2012 | Merchant |
| 2012/0203573 | A1 | 8/2012 | Mayer et al. |
| 2012/0228226 | A1 | 9/2012 | Castellarnau et al. |
| 2012/0232364 | A1 | 9/2012 | Delmage |
| 2012/0310135 | A1 | 12/2012 | Bauer et al. |
| 2012/0316465 | A1 | 12/2012 | Maier et al. |
| 2013/0134077 | A1 | 5/2013 | Wieskotten et al. |
| 2013/0153474 | A1 | 6/2013 | Frorip et al. |
| 2013/0280104 | A1 | 10/2013 | Heide et al. |
| 2014/0012097 | A1 | 1/2014 | McCrea et al. |
| 2014/0224736 | A1 | 8/2014 | Heide et al. |
| 2014/0299544 | A1* | 10/2014 | Wilt ................ A61M 1/1565 417/474 |
| 2015/0005699 | A1 | 1/2015 | Burbank et al. |
| 2015/0100009 | A1 | 4/2015 | Bearss |
| 2015/0133854 | A1 | 5/2015 | Zhu et al. |
| 2015/0164370 | A1 | 6/2015 | Wabel et al. |
| 2015/0258277 | A1 | 9/2015 | Halpert et al. |
| 2015/0320363 | A1 | 11/2015 | Haan |
| 2016/0058933 | A1* | 3/2016 | Ballantyne ............ G06F 21/565 210/85 |
| 2016/0151554 | A1 | 6/2016 | Jansson et al. |
| 2016/0166748 | A1 | 6/2016 | Meyer et al. |
| 2016/0374596 | A1 | 12/2016 | Barrett |
| 2016/0377530 | A1 | 12/2016 | Barrett |
| 2017/0072125 | A1 | 3/2017 | Wallenås et al. |
| 2017/0196517 | A1 | 7/2017 | Zhang |
| 2017/0202493 | A1 | 7/2017 | Bezemer |
| 2017/0224897 | A1 | 8/2017 | Kopperschmidt et al. |
| 2017/0232174 | A1 | 8/2017 | Gerlach et al. |
| 2017/0239409 | A1 | 8/2017 | Reyes et al. |
| 2017/0258979 | A1 | 9/2017 | Fulkerson et al. |
| 2017/0265793 | A1 | 9/2017 | Maierhofer |
| 2017/0281849 | A1 | 10/2017 | Goto et al. |
| 2017/0340801 | A1 | 11/2017 | Roger et al. |
| 2017/0348471 | A1 | 12/2017 | Goto et al. |
| 2018/0055988 | A1 | 3/2018 | Brun |
| 2018/0140761 | A1 | 5/2018 | Rovatti et al. |
| 2018/0169315 | A1 | 6/2018 | Rovatti et al. |

FOREIGN PATENT DOCUMENTS

| | | |
|---|---|---|
| EP | 2279768 A1 | 2/2011 |
| EP | 2388030 B1 | 11/2011 |
| EP | 2558967 A1 | 2/2013 |
| EP | 2656785 A1 | 10/2013 |
| EP | 2678070 A2 | 1/2014 |
| EP | 2730302 B1 | 5/2014 |
| EP | 2734111 A2 | 5/2014 |
| EP | 2735323 B1 | 5/2014 |
| EP | 2836112 A1 | 2/2015 |
| EP | 2670454 B1 | 12/2015 |
| EP | 2578147 B1 | 4/2016 |
| EP | 3145393 A1 | 3/2017 |
| JP | 2004313522 A | 11/2004 |
| JP | 2008264217 A | 11/2008 |
| JP | 2009273749 A | 11/2009 |
| JP | 2009273750 A | 11/2009 |
| JP | 2009297403 A | 12/2009 |
| JP | 2009297404 A | 12/2009 |
| JP | 2009297405 A | 12/2009 |
| JP | 2010029434 A | 2/2010 |

(56) References Cited

FOREIGN PATENT DOCUMENTS

| | | |
|---|---|---|
| JP | 2011047767 A | 3/2011 |
| JP | 4905475 B2 | 3/2012 |
| JP | 5278681 B2 | 9/2013 |
| JP | 5280874 B2 | 9/2013 |
| JP | 5301259 B2 | 9/2013 |
| JP | 5385763 B2 | 1/2014 |
| JP | 5385764 B2 | 1/2014 |
| JP | 5548917 B2 | 7/2014 |
| JP | 2015029882 A | 2/2015 |
| JP | 2016214367 A | 12/2016 |
| WO | 2003028860 A1 | 4/2003 |
| WO | 2011130669 A1 | 10/2011 |
| WO | 2013010677 A2 | 1/2013 |
| WO | 2013152854 A1 | 10/2013 |
| WO | 2012116336 A3 | 2/2014 |
| WO | 2014090746 A1 | 6/2014 |
| WO | 2015007596 A1 | 1/2015 |
| WO | 2015179523 A1 | 11/2015 |
| WO | 2016057982 A1 | 4/2016 |
| WO | 2018017623 A1 | 1/2018 |

OTHER PUBLICATIONS

Communication under Rule 71(3) EPC dated Mar. 18, 2022 for European Patent Application No. 19171893.1.
Office Action (Notice of Reasons for Refusal) mailed Mar. 8, 2022 for Japanese Patent Application No. 2021-007983.
International Search Report and Written Opinion mailed Aug. 4, 2020 for International Patent Application No. PCT/US2020/034420.
Office Action (Notice of Reasons for Refusal) mailed Sep. 27, 2022 for Japanese Patent Application No. 2021-007983.
Extended European Search Report dated Jul. 8, 2022 for European Patent Application No. 22169775.8.
Extended European Search Report dated Apr. 24, 2023 for European Patent Application No. 20809725.3.
Extended European Search Report dated Feb. 3, 2020 for European Patent Application No. 17831728.5.
Extended European Search Report dated Jul. 19, 2019 for European Patent Application No. 19171893.1.
International Preliminary Report on Patentability for PCT/US2015/055031 dated Apr. 11, 2017, including the Written Opinion of the International Searching Authority dated Feb. 26, 2016.
International Search Report and Written Opinion for International Application No. PCT/US2015/055031 dated Feb. 26, 2016.
International Search Report and Written Opinion for International Patent Application No. PCT/US2017/042683 dated Dec. 7, 2017.
International Search Report issued in corresponding PCT/US2017/042683, mailed on Dec. 7, 2017.
Japanese Office Action dated Aug. 20, 2019, issued in Japanese Patent Application No. 2019-502220.
Office Action (Communication Pursuant to Article 94(3) EPC) dated Apr. 19, 2021 for European Patent Application No. 17831728.5.
Office Action (Communication Pursuant to Article 94(3) EPC) dated Mar. 13, 2019 for European Patent Application No. 15790326.1.
Office Action (Decision of Rejection) mailed Sep. 24, 2020 for Japanese Patent Application No. 2019-502220.
Office Action (Examination Report under Section 18(3)) dated Apr. 17, 2019 for UK Patent Application No. 1902215.1.
Office Action (First Office Action) mailed Oct. 19, 2021 for Japanese Patent Application No. 2019-502220.
Office Action (Notice of Reasons for Rejection) mailed Feb. 18, 2020 for Japanese Patent Application No. 2019-502220.
Office Action (Pre-Appeal Examination Report) mailed Mar. 30, 2021 for Japanese Patent Application No. 2019-502220.

* cited by examiner

FLOW SYNCHRONIZATION DEVICES, METHODS, AND SYSTEMS

CROSS-REFERENCE TO RELATED APPLICATIONS

This Application is a U.S. national stage filing under 35 U.S.C. § 371 of International Application No. PCT/US2020/034420, filed May 22, 2020, which claims priority to and the benefit of U.S. Provisional Patent Application No. 62/851,922 filed May 23, 2019, both of which are hereby incorporated by reference in their entireties.

BACKGROUND

A basic function of many extra corporeal blood treatment systems (ECBT systems), including hemodialysis, hemofiltration, hemodiafiltration, apheresis systems, etc., is the maintenance of the overall fluid balance between the fluid added to the patient and the fluid withdrawn from the patient. Ideally, this exchange will result in a net loss or gain of fluid to/from the patient that precisely matches the patient's treatment requirement. To achieve this, the ECBT may employ a volumetric fluid balancing system, of which a variety of different types are known. For example, see U.S. Pat. Nos. 5,836,908, 4,728,433, 5,344,568, 4,894,150, and 6,284,131, each of which is hereby incorporated by reference as if fully set forth in their entireties herein.

Fluid balancing mechanisms generally attempt to ensure that the total mass or volume of fluid pumped into, and removed from, the non-blood side of a filter or dialyzer are equal. To provide for a desired differential between the net quantity removed/added, the inflow and outflow rates can be controlled to produce a net difference. This may be provided by regulating the relative flow rates generated by inflowing and outflowing pumps or by using a separate bypass, driven by a separate pump. In an example, such a bypass pump pumps at an ultrafiltration ("UF") line rate which is added to the balanced withdrawal rate.

Gravimetric systems that balance flow by weighing mass from a source and collected fluid from the treatment device and comparing the two are known. Another approach is to measure incremental volume transfer. Hard plumbed or disposable lined balance chambers alternately fill and empty in a manner that assures equal and opposite volume exchange. Systems using this approach are balancing a single inlet fluid flow with an effluent stream. A second stream of fluid is frequently added to the extracorporeal circuit using an additional pump, or external IV pump. The volume of this second stream may be balanced by the isolated ultrafiltration (UF) pump in an attempt to maintain patient fluid balance. This approach is limited by the calibration inaccuracies of the additional or external pump and the isolated UF pump. These inaccuracies are acceptable at low flow rates. However, at higher flow rates the cumulative volumetric inaccuracies may not achieve the desired patient volumetric balance. Additionally, this approach requires an operator to independently set the pump rates to achieve the desired balance.

SUMMARY

The disclosed subject matter described in this disclosure is an alternate approach to volumetric fluid balance using multiple volumetric or fixed-displacement pumps to control inflows and outflows from an extracorporeal circuit that have corresponding pump rates synchronized relative to each other to assure balanced flow rates.

In certain systems, volumetric fluid balancing may be performed for a single therapy fluid stream using a system configuration including balance chambers, peristaltic pumps, and mechanically controlled pinch valves. The therapy fluid entering the blood path of the extracorporeal circuit may be balanced with effluent removed from the blood path through the dialyzer of the circuit so that the patient volume is not affected by this exchange of fluids. The limitation to a single therapy fluid inlet flow is a common limitation of various dialysis machines that use balance chambers. Some extracorporeal therapies can use more than one therapy fluid inlet flow that may be volumetrically controlled to achieve an overall patient fluid balance. For example, the difference between the total fluid that moves into the patient (for example, by flowing into the patient's blood stream) and that withdrawn from the patient must be precisely controlled. For example, in dialysis treatment, the amount of fluid entering the patient, for example through pre-dilution, post-dilution, citrate infusion, and reverse ultrafiltration streams may be balanced against the net ultrafiltration stream to achieve a target net ultrafiltration rate. The subject matter described in this disclosure provides alternate machine configurations that support one or more therapy fluid flows synchronized with the effluent fluid flow from the extracorporeal circuit to achieve accurate fluid balance.

The disclosed subject matter includes several different system configurations that support one or more therapy fluid inlet flows balanced with the effluent flow by diverting each therapy flow pump individually using a valving/flow diversion mechanisms that flow fluids, including blood and/or treatment fluid treatment configuration into a series configuration in which fluid is pumped from one pump to another and the pumping rates synchronized using an imbalance detection device. One imbalance detection is the change in weight of fluid accumulating due to back-up of fluid between a faster upstream pump and a slow downstream pump. Another imbalance detection is the pressure buildup due to fluid volume accumulation caused by back-up of the flow. In other embodiments, pumps are individually calibrated at relevant times (one or more times per treatment for example) against a common or gold standard flow rate measurement device. In still other embodiments, imbalance is detected during treatment without establishing a special configuration by directly measuring the flow rates of fluid, directly by flow measurement or indirectly by measuring pressure changes to infer balanced or imbalanced flow conditions from a temporal trend which can be predict the magnitude of imbalance. For example, one of the pumps can be incrementally stepped, the pressure change or fluid weight trend sampled for a period of time for each step, to establish a trend, and perfect balance fitted to the trend in order to back out the synchronized flow rates arithmetically. Any type of fitting function may be used such as a straight line or polynomial. When pumps are synchronized, the operating condition are maintained to ensure the synchronization conditions, for example suction pressure, are comparable to those during synchronization.

In embodiments, reliable flow balance is obtained by synchronizing the pump flows and using the pressure sensor to synchronize the rates rather than enforcing a fixed-volume flow channel. A controller connected to the pressure sensor and pumps adjusts the effluent flow pump to the desired flow rate and the selected therapy fluid flow pump to achieve a desired pressure between the pumps and holds the pressure stable for a period of time to achieve a synchronization flow value for the therapy fluid pump. This can be repeated for one or multiple inlet pump pressure values and stabilization times to achieve a synchronization curve for the therapy fluid flow pump versus pressure. Alternatively, it can be done for a single condition that is to be maintained during treatment. If the system needs to change operation state due to an uncontrolled change such as a change of flow resistance of a patient access or a controlled change such as a shift to a lower or higher flow rate, new synchronization at the new condition may be performed. Once synchronized, small excursions from the synchronized condition that occur thereafter, for example during treatment, will be adjusted-for, such as when the rates of the pumps that were synchronized during synchronization are varied from their absolute or relative operating speeds, for example to provide a selected ultrafiltration rate. The accommodation is provided by continuously performing pump pressure compensation, which refers to recalculating the relationship between the commanded flow rate (or equivalent such as shaft speed or cycle rate depending on the type of pump) and estimated actual flow rate based on known or measured pump curves. The pump curves may represent flow versus outlet minus inlet pressure (pressure differential) or flow versus inlet pressure only. Other variations are possible depending on the type of pump. In variations, the synchronization process may be triggered by change in arterial pressure, blood treatment device blood side pressure, blood treatment device treatment fluid side pressure, or after a time interval. Such triggered synchronizations may be done for prescribed (i.e., predefined) blood and treatment fluid flow rates only so that a synchronization process over multiple conditions is not required. This "spot synchronization" process is particularly relevant in combination synchronization processes where no bypass flow is established so that treatment does not have to be significantly disrupted as described below with reference to FIG. 8, for example. Synchronization may be done during a priming operation, during treatment, or both. Spot synchronization may be done after a period of time over a treatment as well. The reason for triggering a synchronization after a period of time in the absence of any other change may be, for example, changes in material properties over time or due to extended use, for example a plastic pumping tube segment may exhibit changes in characteristics over continued use during a treatment. Thus to maintain accuracy of balancing, a synchronization may be performed after a time estimated to ensure that the amount of change is limited.

In embodiments, rather than continuously or repeatedly readjusting the flow rates of pumps to compensate for inlet pressure variation, the cumulative error caused by variations in pumping rates over a treatment interval are calculated and stored over time. Then the pumping rates are adjusted at a single time (at several times) for a calculated period of time to compensate for the impact of the error on total ultrafiltration that occurred over the treatment interval. The stepwise correction may be done in a single operation at one time toward the end of a single treatment interval or multiple times over multiple treatment intervals into which a single treatment session is divided. These operations may be done automatically without operator intervention. The treatment intervals may be defined according to events such as shut-downs due to automatic alarms or operator commands. For example, the pumping rates may be adjusted according to cumulative effect of error prior to a shutdown by adjusting the pumping rates immediately after restart. Also, compensation by adjusting the pumping rates can be done multiple times at regular intervals or at other predefined times during a treatment.

Once synchronized, the pumping rates may be changed to implement a predefined difference in commanded pump speeds according to a stored pump curve. The pump curve is not limited to a stored formula or algorithm but may also be implemented as a look up table or equivalent. The difference in commanded pump speeds is adapted to provide for a prescribed or otherwise provided ultrafiltration rate. The different speeds may provide for a desired fluid balance outcome in the extracorporeal circuit (neutral, positive, or negative balance). In embodiments, the difference in speed may be limited to a minor fractional difference (i.e., less than 50% speed difference) and may be limited to fractional differences of less than 20% or 10% to ensure and improve accuracy during treatment. In any of the embodiments, the synchronization may include multiple flow, for example, a pre-dilution flow of replacement fluid which would flow into a patient's blood during treatment, plus a fresh dialysate flow and synchronized with a flow of waste. As indicated, the pump rates may be further compensated to account for transient effects such as changes in inlet/outlet pressures, changes due to pump life, and other factors. A compliant accumulator or additional tubing lengths can be used to reduce pressure spikes and aid in achieving stable pressure control during the synchronization process.

The embodiments are applicable to synchronization of series (serially) interconnected through a treatment device) blood pumps or series treatment fluid pumps. In embodiments, direct flow between the series pumps is provided by halting flow through lines that exchange fluid with the flow path connecting the series pumps to be synchronized. For example, two series blood pumps connected to a filter have a fixed volume path between them when flow through lines connected to the non-blood side is prevented, such as by halting one or more treatment fluid pumps, clamping one or more treatment fluid lines, or both. For another example, two series treatment fluid pumps connected to a filter have a fixed volume path between them when flow through lines connected to the blood side is prevented, such as by halting one or more pumps, clamping one or more blood lines, or both. The fixed volume can be implemented by any suitable means for halting flow on the other side (other side of the pumps used for balancing) of the treatment fluid device including halting inflow and outflow pumps on said other side or halting a single pump such as an inflow pump and clamping the other line, such as an outflow line. These may depend on the configuration.

All pumps may be equipped with an inlet pressure sensor and may also be fitted with an outlet pressure sensor to support pressure compensation of the pump rate. In a pressure compensation method, the flow rate of the pump may be derived from the pump rotation or reciprocation rate and adjusted responsively to the inlet and/or outlet pressure. This derivation and compensation may be done using a single function of both pressure (inlet, outlet, oncotic, or pressure change) and rotation speed. For example, the function may be embodied in a look up table stored in a data store of a controller. Additionally, the control valves may be closed so that pump occlusion may be confirmed by the reading of the various pressure sensors.

In embodiments, flow is halted in the non-blood compartment of a treatment device and an average blood compartment pressure is established by flowing fluid through the blood compartment of the treatment device by pumping fluid into the blood compartment and with a predefined resistance at the outlet of the blood compartment. This average pressure is stored as a target. The dialysate compartment pressure is affected by the oncotic pressure caused by the presence of protein in the blood. Fresh and waste treatment fluid pumps connected to the non-blood compartment are then synchronized by commanding the waste treatment fluid pump to a predefined treatment fluid flow rate and adjusting the fresh treatment fluid pump rate until the target average blood compartment pressure is restored in the blood compartment. In alternative embodiments, the target may be established from the treatment fluid pressure (e.g., taking an average of the inlet and outlet treatment fluid pressure at the inlet and outlet ports of the treatment fluid device). By measuring the difference between treatment fluid device treatment fluid compartment pressure and blood compartment pressure during zero (or near-zero) transmembrane flow conditions, oncotic pressure may be directly determined. The technique may be used to determine the oncotic pressure which may be used as well for other purposes, such as determining the magnitude of ultrafiltration required (i.e., how much excess fluid is in the patient's blood—hypervolemia). The synchronized fresh treatment fluid pump rate is recorded. This procedure may be repeated for multiple predefined pumping rates and blood compartment pressures to record a table of blood compartment average pressures and predefined treatment fluid flow rates as the independent variables (e.g., rows and columns although any data storage element may be used) and a corresponding synchronized fresh treatment fluid flow rate for each combination (e.g., recorded in the cells of the table). The data may be fitted to a function to estimate a synchronized fresh treatment fluid pumping rate for any prescribed combination of treatment fluid flow rate and blood flow rate through the blood compartment, which will correspond, during treatment, to an average pressure of the blood compartment. When treatment is performed, the average blood compartment pressure is measured and applied to the fitted function, with a prescribed treatment fluid flow rate, to obtain an estimated fresh treatment fluid flow rate. A modified waste treatment fluid flow rate is then calculated to provide for a prescribed ultrafiltration rate. The pumping rate of the waste treatment fluid flow rate may be generated from a function of inlet pressure and target flow rate that provides a command flow rate to be applied to the pump. Such functions are commonly used for controlling peristaltic pumps. The step in commanded flow required by the waste treatment fluid pump to achieve the required ultrafiltration may be calculated from such a function and the current waste treatment fluid inlet pressure, then the waste treatment fluid pump commanded correspondingly. The new inlet pressure may be fed back iteratively to obtain a refined command flow for the waste treatment fluid pump until the inlet pressure stops changing within a predefined interval. Whenever, during treatment, the average blood compartment pressure changes beyond a predefined threshold, the fresh treatment fluid pump rate may be adjusted to return the average blood compartment pressure to the target and the waste treatment fluid pump rate reestablished iteratively as above. If the average blood compartment pressure changes beyond a greater threshold, the fresh treatment fluid pumping rate may be recalculated based on the prescribed treatment fluid flow rate as above and the waste treatment fluid pumping rate adjusted iteratively as above based upon a prescribed ultrafiltration rate.

The principles of the subject matter disclosed herein are applicable to both peristaltic pumps with disposable fluid pathways as well as hard plumbed systems and combinations of the two. In a hard plumbed configuration, the flow path components may require disinfection similar to standard dialysis machines and would require special techniques to meet the requirements for direct infusion of therapy fluids.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Some of the figures may have been simplified by the omission of selected features for the purpose of more clearly showing other underlying features. Such omissions of elements in some figures are not necessarily indicative of the presence or absence of particular elements in any of the exemplary embodiments, except as may be explicitly disclosed in the corresponding written description.

DETAILED DESCRIPTION

Figure 1:
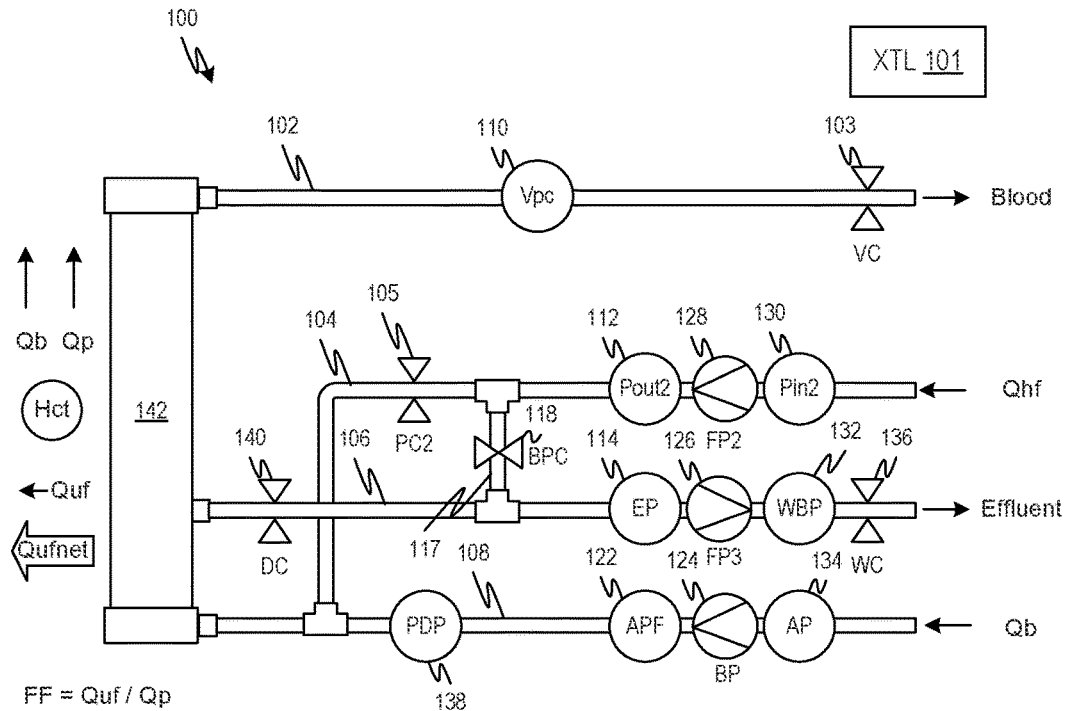
FIG. 1 shows a hemofiltration system with instrumentation for measuring pressure according to embodiments of the disclosed subject matter.

Referring to FIG. 1, a hemofiltration system 100 is shown in a treatment mode. Blood is pumped through an arterial blood line 108 at a selected flow rate by a blood pump 124. A pump inlet pressure is indicated by a blood pump inlet pressure sensor 134. A blood pump outlet pressure is indicated by a blood pump outlet pressure sensor 122. A pre-hemofilter blood pressure immediately upstream of a hemofilter 142 is indicated by a pre-hemofilter blood pressure sensor. Replacement fluid is pumped by a replacement fluid pump 128 through a replacement fluid line 104 into the arterial blood line 108 at a selected rate by a replacement fluid pump 128. Replacement fluid pump inlet and outlet pressure sensors 130 and 112, respectively, indicate replacement fluid pump inlet and outlet pressures, respectively. The replacement fluid is combined with blood before it enters the hemofilter 142. In alternative embodiments, the replacement fluid flows into a venous blood line 102 after passing through the hemofilter 142. The pressure in the arterial blood line is indicated by a venous pressure sensor 110. A bypass line 117 selectively conveys replacement fluid directly to an effluent line 106. Waste from the hemofilter 142 is conveyed through the effluent line 106 by an effluent pump 126. Effluent pump inlet pressure sensor 114 and effluent pump outlet pressure sensor 132, respectively, indicate effluent pump inlet and outlet pressures. A pre-hemofilter pressure sensor 138 indicates pressure immediately upstream of the hemofilter 142.

All line clamps are controlled by a controller 101. All sensors apply corresponding signals to the controller 101. A venous clamp 103 selectively allows and stops flow through the venous blood line 102 under control of the controller 101. A replacement fluid clamp 105 selectively allows and stops flow through the replacement fluid line 104 under control of the controller 101. A bypass clamp 118 selectively allows and stops flow through the bypass line 117 under control of the controller 101. An effluent clamp 140 selectively allows and stops flow through the effluent line 106 under control of the controller 101 between the hemofilter 142 and the bypass line 117 while a waste clamp 136 selectively allows and stops flow downstream of the effluent pump 126 also under control of the controller 101.

Background on the presented technology may be found in International Patent Application WO 2018017623, filed Jul. 18, 2017, incorporated herein by reference as if fully set forth in its entirety. The purpose of the presented technology for balancing fluid flow and synchronization of inflow and outflow pumps is to provide for fluid balance and the achievement of a target ultrafiltration over the course of a treatment. The basis for establishing volumetric balance is by synchronization (synch) of the hemofiltration pump to the hemofilter and the outlet effluent pump. The system is designed to balance two streams with this method to provide hemofiltration (HF).

For hemofiltration, synchronization occurs through the bypass fluid line 117. A first sync target pressure is obtained by obtaining the effluent inlet pressure measured when the blood pump is at a desired flow rate and the hemofiltration pump and effluent pumps are off. Hemofiltration creates such a large difference at the effluent pump inlet when the pumps are on compared to the pressure when pumps are off, a second synch can be performed to meet accuracy specifications. The target pressure for the second sync is the effluent pump inlet pressure measured when the blood pump is at the desired flow rate with the pumps are set to the rates determined in the first sync.

The system may use peristaltic pumps for all pumping requirements. These pumps result in pulsatile flows and pressures at the inlet and outlets of the pumps. Depending on rates and compliance of the tubing at the pump inlets and outlets this pulsatile flow can produce noisy pressure signals. For use in the synchronization process, these signals may be electronically filtered by a low pass filter.

The peristaltic pump output for a fixed rotor revolution is impacted by the inlet pressure and tubing segment life and to a lesser extent the outlet pressure and fluid temperature. The system includes compensation algorithms to minimize the influence of these variables.

Figure 2:
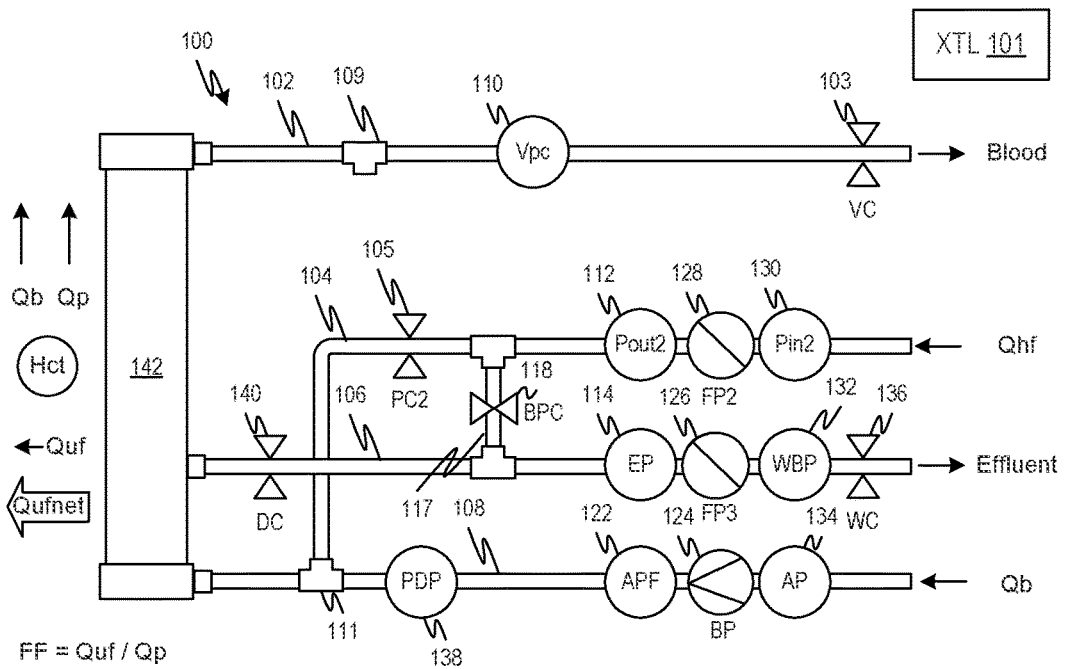
FIG. 2 shows the system of FIG. 1 in a mode for establishment of a synchronization target according to embodiments of the disclosed subject matter.

FIG. 2 shows the system of FIG. 1 in a configuration for obtaining a target pressure for a first synchronization of inlet and outlet flow pumps, the effluent pump 126 and the replacement fluid pump 128. In this configuration both the inlet and outlet flow pumps, the effluent pump 126 and the replacement fluid pump 128 are halted thereby occluding flow from and to the hemofilter 142. The bypass clamp 118 is also closed so that no flow occurs into or out from the hemofilter 142 except for blood flow in the arterial and arterial blood lines 108 and 102, respectively. The venous clamp 103 is opened and the waste clamp 136 is closed. The effluent clamp 140 is open so that pressure from the hemofilter 142 is detected by the effluent pump inlet pressure sensor 114.

Pump pressure compensation is a kind of pump control where the rate of the pump is controlled responsively to the inlet pressure of the pump according to an algorithm. The algorithm compensates the relationship between the commanded rate and the actual flow rate. In the process discussed with regard to FIG. 2, pressure compensation is turned off so that the rate of flow is presumed to be governed strictly by the speed of the pump actuator.

The blood pump 124 is set to a desired flow rate Qb, that is, a flow rate that the system is intended to operate at after the synchronization process is completed. Then the effluent pump inlet pressure sensor 114 pressure indication is read. An average of the pressure signals from venous pressure sensor 110 and the pre-hemofilter pressure sensor 138 is used to obtain an average blood pressure in the hemofilter 142 (AvePb). The system waits a predefined number of seconds (Tstabilize) for AvePb to stabilize (cease varying within a predefined range) and then takes the average of the effluent pump inlet pressure sensor 114 indication over a period of Tstabilize seconds (EP1). The AvePb over Tstabilize seconds and the AvePb are used to measure oncotic pressure (Po) which is equal to the difference between AvePb and EP1, i.e., Po=AvePb−EP1. In the configuration of FIG. 2, called pre-dilution. Note, post-dilution is where replacement fluid is fed into the venous blood line 102 instead of the arterial blood line 108. In alternative embodiments, replacement fluid is introduced in a fashion identified as post-dilution in which the replacement fluid line 104 may be connected to a junction 109 instead of the junction 111. A hemofilter exit oncotic pressure of blood (Poe) is calculated as Po in the pre-dilution configuration. In the post-dilution configuration Poe is determined from $$Poe = 2.1*Ce + 0.16*Ce^2 + 0.009*Ce^3 \quad \text{[the Landis-Pappenheimer equation]};$$

where $Ce = Ci*Qp/(Qp-Qhf)$;
$Ci$ is the solution to $Po-(2.1*Ci+0.16*Ci^2+0.009*Ci^3)=0$
$Qp$ is the plasma flow range given by:
For the post-dilution configuration, $$Qp = Qb*(1-Hct)$$

where Hct is the hematocrit for the post-dilution
For the pre-dilution configuration, $$Qp = Qhf + Qb*(1-Hct)$$

where Qhf=the replacement fluid flow rate
Qb is the blood flow rate
Note that Hct may be taken as 0.3 if not known. Note also that there is a known relationship of the Oncotic pressure as a function of plasma protein concentration may be employed in embodiments. The known relationship is called the Landis-Pappenheimer equation.

Figure 3:
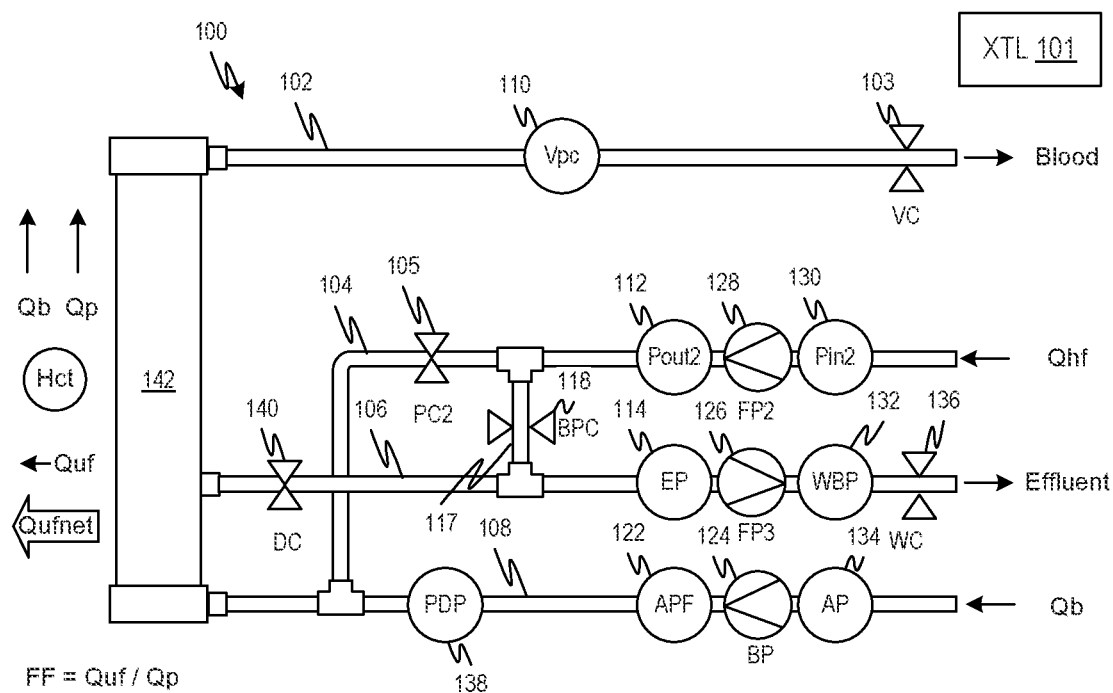
FIG. 3 shows the system of FIG. 1 in a mode for establishment of a pump synchronization according to embodiments of the disclosed subject matter.

Referring now to FIG. 3, the hemofiltration system 100 configuration is changed such that the blood pump 124 keeps running and replacement fluid pump 128 and effluent pump 126 are run according to a specific procedure now described. The bypass clamp 118 and the waste clamp 136 are opened and the replacement fluid clamp 105 and the effluent clamp 140 are closed. Thus, replacement fluid is pumped by replacement fluid pump 128 through the bypass line 117 into the effluent line 106. This connects the replacement fluid pump 128 and effluent pump 126 in series. For effluent pump 126 pressure compensation is turned off. The effluent pump 126 is set to a desired flow rate and the replacement fluid pump 128 is adjusted until the pressure indicated by effluent pump inlet pressure sensor 114 reaches the value EP1. After Tdone seconds of control, the replacement fluid pump 128 commanded pumping rate is averaged for TavePer seconds and set equal to the synched rate for that pump with effluent pump 126 running at the selected commanded rate. The pressure indicated by effluent pump inlet pressure sensor 114 is averaged over TavePer and set equal to the EP1 reference pressure (EP1ref).

Figure 4:
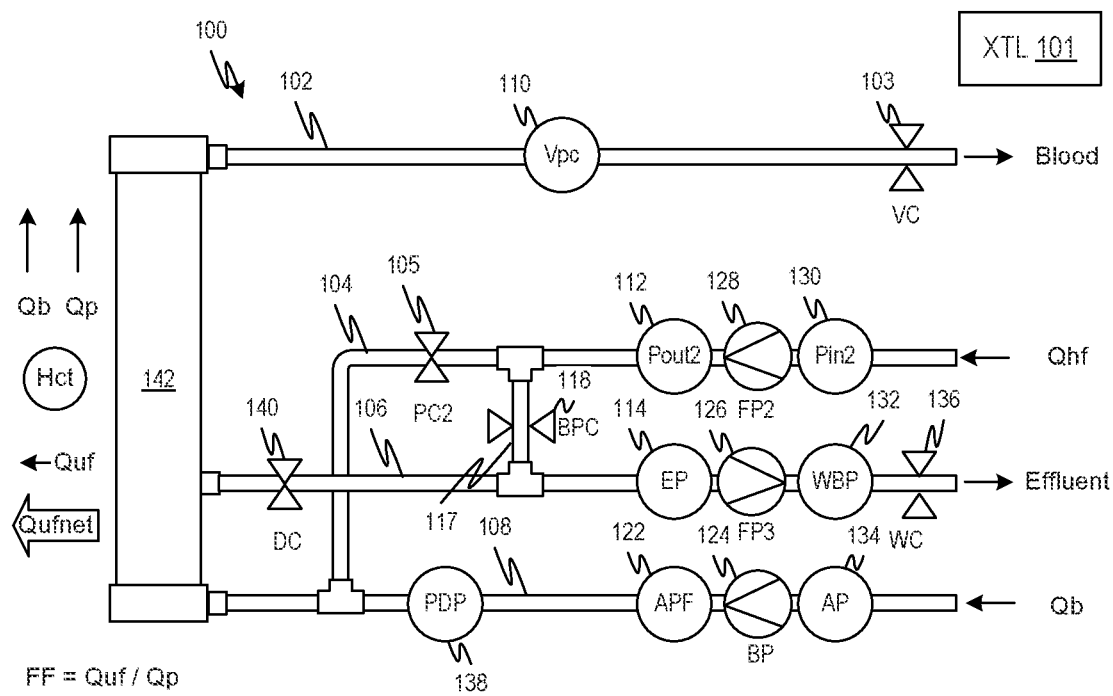
FIG. 4 shows the system of FIG. 1 in a mode for determining a synchronization parameter according to embodiments of the disclosed subject matter.

Under certain conditions, a second synchronization is done as indicated above. In certain circumstances instead of a second synchronization being done, the following procedure is performed. Referring to FIG. 4, the replacement fluid clamp 105 and the effluent fluid clamp 140 are opened and the bypass clamp 118 is closed. The pressure compensation algorithm is used to control the effluent pump 126 according to the following equation:

$$FP3c = HFd*(1+(\text{icompf})*(Poe-Po) - (\text{icompf})*(EP-EP1\text{ref})),$$

where HFd is the desired replacement fluid flow rate and icomp (same as icompf for hemofiltration) is the inlet pressure compensation coefficient determined by a procedure at HFd in which a synchronization is performed at AvePb. Once replacement fluid pump 128 and effluent pump 126 are synchronized, the rate of replacement fluid pump 128 is perturbed first to a higher speed than the synchronized one and then to a lower speed than the synchronized one. At each point, the equilibrated pressure is recorded after a predefined interval to obtain three pressure vs commanded flow rate data points. These three data points are fitted to a straight line with pressure on the Y axis and flow rate on the X axis. The slope is divided by the effluent pump 126 commanded flow rate to obtain icomp.

Figure 5:
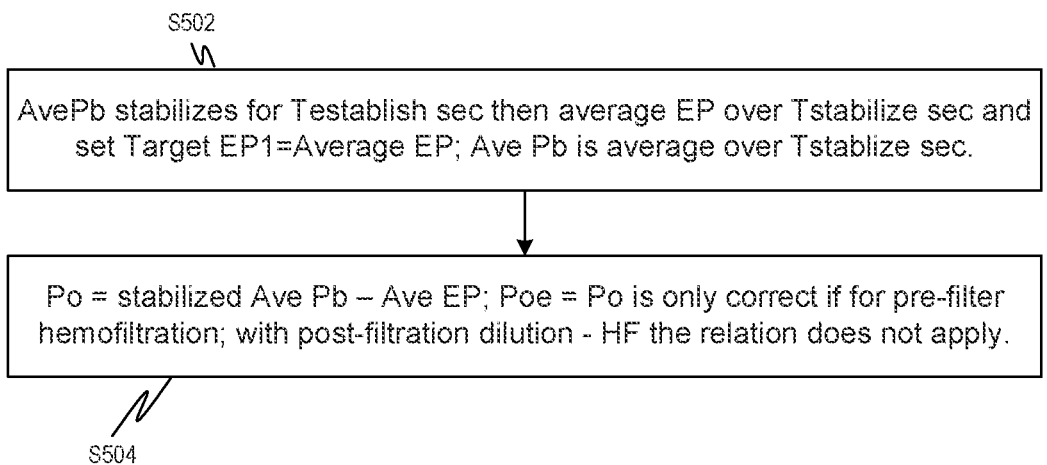
FIGS. 5, 6, 7, and 8 show flow charts of operations of the embodiments of FIGS. 2-4.

FIG. 5 summarizes the procedure described with reference to FIG. 2. EP stands for effluent pressure and is given by the effluent pump inlet pressure sensor 114. The procedure of FIG. 5 includes steps S502 and S504, and can be done at certain intervals or upon certain events, such as after the lapse of a predefined period of time, when a fluid circuit is changed or one of the pump speeds are changed, such as the blood pump or hemofiltration fluid pump.

Figure 7:
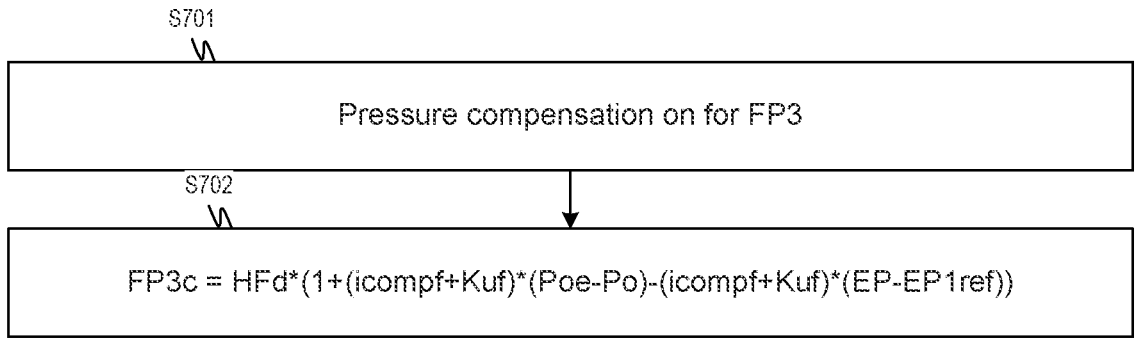
Figure 8:
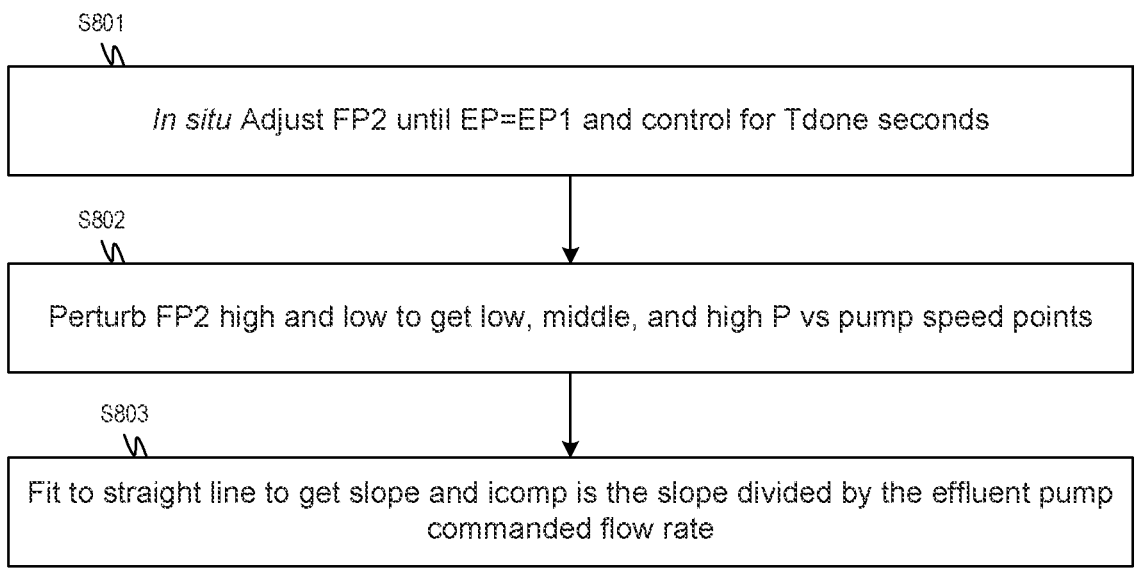

FIG. 8 shows a procedure at S801 like that of FIG. 5, namely a synchronization of pumps, however in this case, the replacement fluid pump 128 (FP2) speed is perturbed at S802, (i.e., increased and also decreased), and speed and effluent pump 126 inlet pressure given by effluent pump inlet pressure sensor 114 are recorded to obtain three data points of pressure versus pump speed. One data point is at the reduced speed. Another data point is at the increased speed. And the third data point is at the normal speed. This procedure yields a parameter icomp (icompf for hemofiltration) at S803 which is used in the procedure of FIG. 7 in the equation for FP3c. Note that FP3 refers to the effluent pump 126. The calculation of icompf is described above.

The out of loop synchronization which is the same as that of FIG. 3, 5, may be done on a different schedule or upon different events that the regular first synchronization with the additional steps of perturbing the flow rate of the replacement fluid pump 128. Once each instance of the out of loop synch is performed, the icompf may be used to obtain the effluent pump 126 (FP3) compensation coefficient. The process is labeled as out of loop sync. For the first part of the formula first part of the algorithm, the next few steps are geared towards determining the effluent pump inlet pressure compensation coefficient in situ.

Note in the discussion of FIG. 8 above, it should be understood that although the algorithm is identified as out of loop synchronization that this is true for the first part of the algorithm but not the next. Rather the next few steps are geared towards determining the effluent pump inlet pressure compensation coefficient in situ, as opposed to out of loop.

Figure 6:
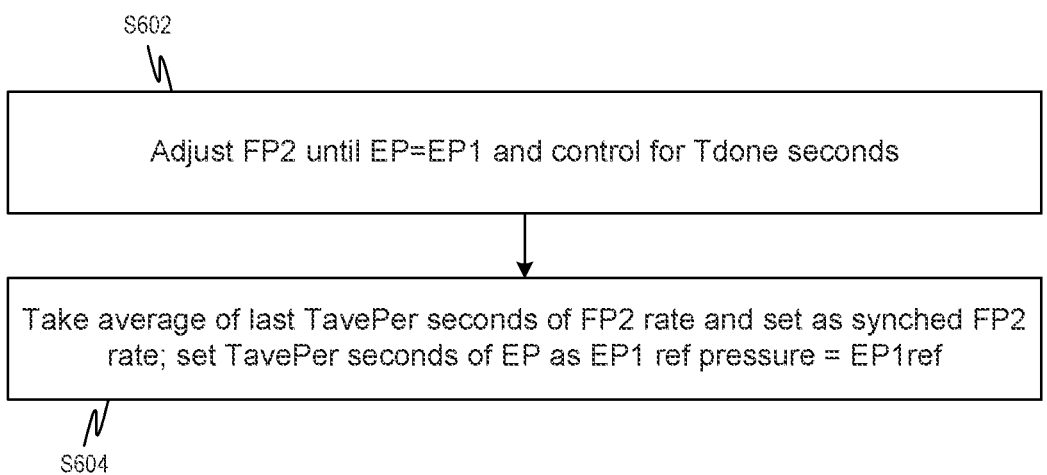

FIG. 6 summarizes the synchronization procedure described with reference to FIG. 3, and includes steps S602 and S604.

FIG. 7 summarizes the procedure described with reference to FIG. 4 which is an out of loop synchronization, and includes steps S701 and S702, as shown in the figure.

Figure 9:
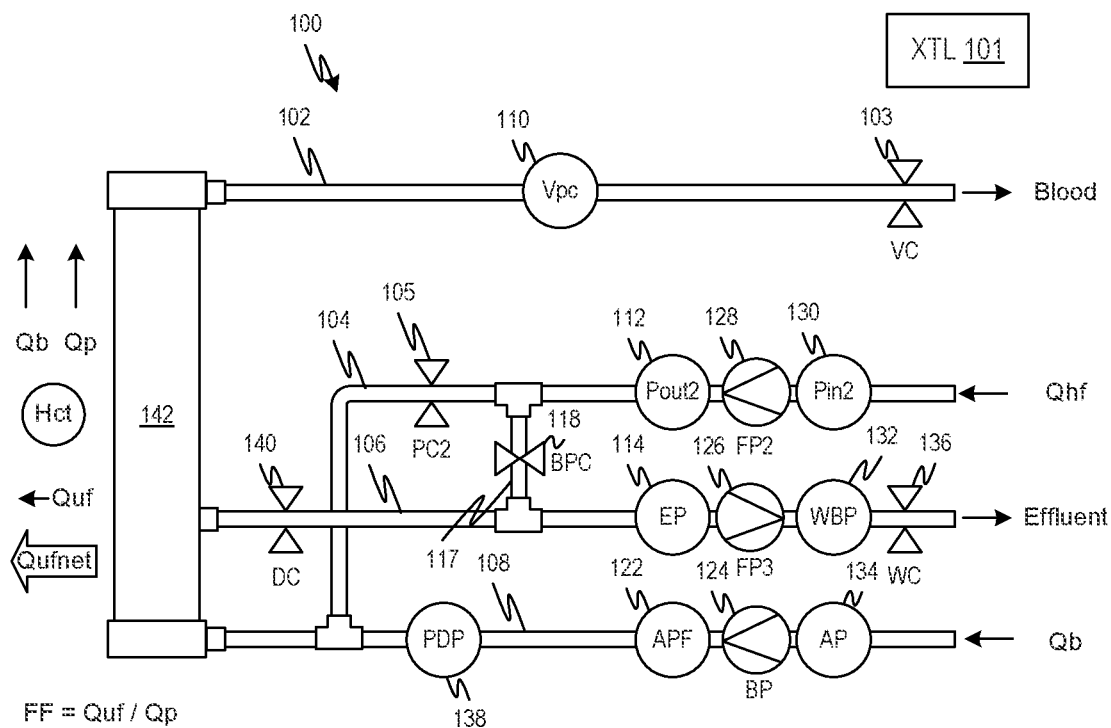
FIG. 9 shows the system of FIG. 1 in a mode for a second synchronization procedure, according to embodiments of the disclosed subject matter.

FIG. 9 shows the configuration of the hemofiltration system 100 for establishing a second synchronization target. In this configuration, the flow of replacement fluid is through the hemofilter 142 and the pumping rates are the synchronized rates of effluent pump 126 and replacement fluid pump 128 found by the first synchronization procedure. The effluent pressure indicated by effluent pump inlet pressure sensor 114 is averaged and stored as a target EP2. Then the bypass configuration, identical to FIG. 3, is assumed by the hemofiltration system 100 and a second synchronization is performed using EP2. This is now described in a complete procedure at FIG. 10.

Figure 10:
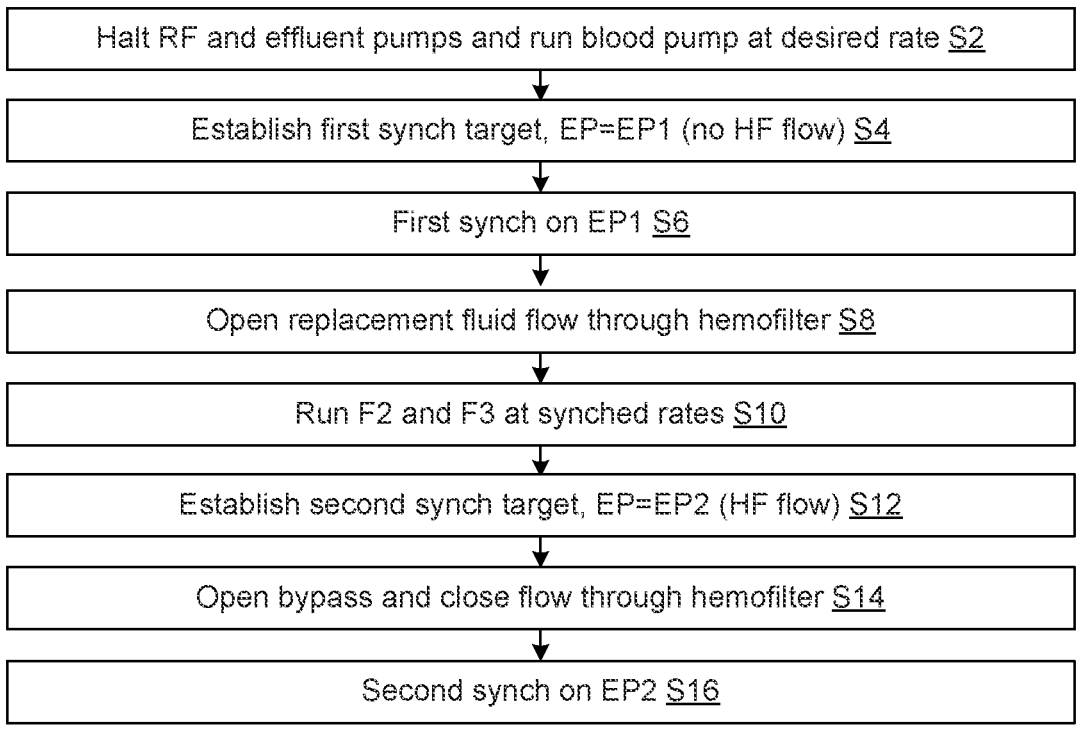
FIG. 10 shows a procedure for performing a first and second synchronization, according to embodiments of the disclosed subject matter.

Referring now to FIG. 10, at S2, the replacement fluid pump 128 and effluent pump 126 are halted and the blood pump 124 is run at a desired rate. The pressure given by effluent pump inlet pressure sensor 114 is averaged as described above and stored as a first target pressure EP1 S4. At S6, a synchronization procedure is performed using the target EP1 to obtain a synchronization coefficient for replacement fluid pump 128 that synchronizes it to effluent pump 126. At S8, the bypass clamp 118 is closed and the replacement fluid pump 128 and at S10 the effluent pump 126 are run at the rates obtained during S6. This causes the replacement fluid to flow through the hemofilter 142. At S12, the pumps are run for a period of time and the effluent pressure from effluent pump inlet pressure sensor 114 averaged to obtain a new target EP2. At S14, flow is established through the bypass line 117 by opening the bypass clamp 118 and closing replacement fluid clamp 105 and a synchronization is performed at S16 using the new target pressure EP2. That is, the rate of FP2 at which the flow balances with FP3 is determined and stored as a coefficient. The EP2 is also used as a reference point for pressure compensation.

Figure 11:
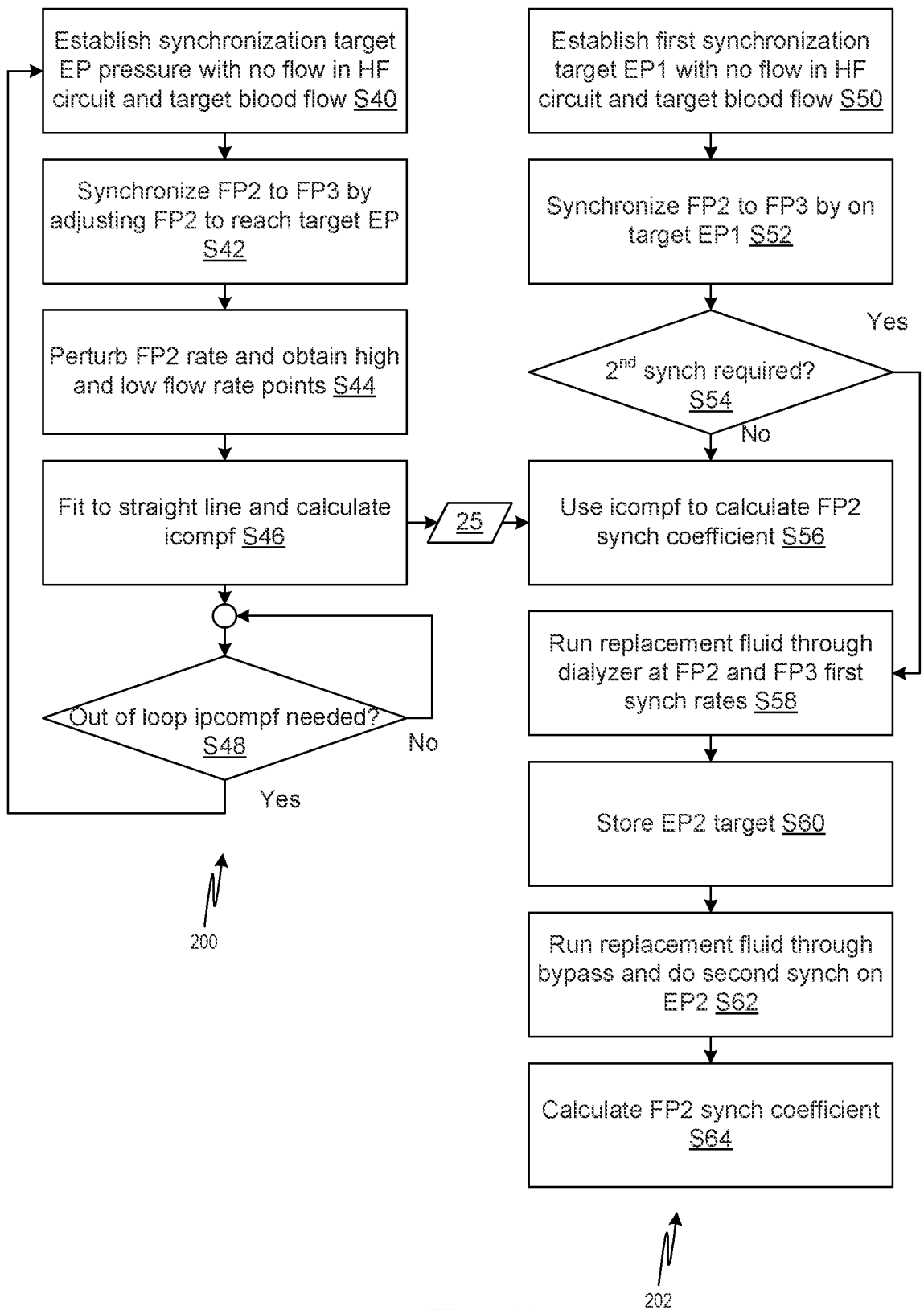
FIG. 11 shows a flow diagram for a conditional synchronization procedure according to embodiments of the disclosed subject matter.

Referring now to FIG. 11, a relationship between out of loop synchronizations and conditional one and two synch procedures is shown. An out of loop procedure is shown at 200 and a synchronization procedure is shown at 202. Data 25 is passed to the synchronization procedure for use in S56 as will described. In the out of loop procedure 200, at S40, the synchronization target is established just as EP1 is obtained as described above and at S42, a synchronization is done as described above based on EP1 as the target. At S44, before finishing the synchronization procedure, the replacement fluid pump 128 rate, which is now synchronized, is increased and decreased above and below the synchronized rate and the effluent pump inlet pressure sensor 114 pressure is recorded for each perturbed rate. This gives rise to three pressures, EP1 and the pressures corresponding to the two perturbed rates. The three points are fitted, at S46 and the value of icompf computed (See FIG. 8 and associated text) and stored (represented as data 25). At S48 it is determined whether icompf should be recalculated or not and if so, control reverts to S40 otherwise it loops to S48.

Continuing to refer to FIG. 11, at S202 the procedure for synchronization begins at S50 with the establishment of a first effluent pressure target EP1 taken as an average of effluent pump inlet pressure sensor 114 as discussed above. At S52 a first synchronization is performed as discussed. At S54 it is determined if a second synchronization is required. Under certain conditions, for example when the replacement fluid flow rates are above a predefined threshold, a second synchronization may not need to be performed and sufficient accuracy can be obtained using the operation S56 in which icompf is used to calculate the synch coefficient rather than going through the whole procedure of S58-S64. If a second synchronization is required, the control proceeds to S58 and replacement fluid is run through the dialyzer with the pre-hemofilter pressure sensor 138 and effluent pump 126 run at the synchronized rates found in S52. The second synchronization target EP2 is stored at S60 and used at S62 to perform a synchronization through the bypass line 117. At S64, the synch coefficient for replacement fluid pump 128 is then calculated and used with pressure compensation to perform treatments until updated again.

According to first embodiments, the disclosed subject matter includes a method of controlling pumps in a hemofiltration system. The method includes connecting inlet and outlet pumps in series and pumping while measuring a pressure within a connecting channel therebetween, sampling the pressure until it stabilizes within a predefined interval. The method includes varying the inlet pump speed until the pressure reaches a predefined target. The method includes changing the inlet pump speed incrementally above and below the speed at which the pressure reached the predefined target and recording inlet pump speed and pressure for the two speeds. The method includes fitting a line to the predefined target pressure and the inlet pump speeds at the above and below incrementally different speeds. The method includes deriving a parameter from the slope of the fitted line and using thereafter to control the inlet pump speed.

In variations thereof, the first embodiments include ones in which the inlet pump pumps replacement fluid into a blood line. In variations thereof, the first embodiments include ones in which the outlet pump withdraws waste fluid from a hemofilter. In variations thereof, the first embodiments include ones in which the predefined target pressure is obtained by measuring the pressure in the waste compartment when there is no flow across the membrane of the hemofilter and while blood is flowing such that a predefined average pressure exists on the blood side of the hemofilter. In variations thereof, the first embodiments include ones in which the predefined average pressure on the blood side is measured at a selected blood pumping speed.

According to second embodiments, the disclosed subject matter includes a method for controlling flow in a fluid circuit. The method includes, in a hemofiltration machine with a controller that controls a net ultrafiltration by independently regulating the speed of a waste pump that draws fluid from a hemofilter and the speed of a replacement fluid pump that pumps replacement fluid into a patient blood line, using the controller to control the pumps to implement synchronization and treatment modes. in the synchronization mode, the controller detecting a target pressure at an inlet of the waste pump while flowing blood through the hemofilter and while blocking flow through the replacement fluid and waste pumps. The method includes subsequently, in the synchronization mode, the controller connecting the replacement fluid pump and the waste pump directly in series and, while flowing replacement fluid between them and controlling the waste pump speed to establish a predetermined hemofiltration rate, controlling the replacement fluid pump speed to determine a synchronized replacement fluid pump speed that maintains the waste pump inlet pressure at said target pressure. The method includes subsequently, in a treatment mode, the controller connecting the replacement fluid pump to pump replacement fluid into a blood circuit at said synchronized replacement pump speed.

According to third embodiments, the disclosed subject matter includes a system for controlling flow in a fluid circuit. A hemofiltration machine as a fluid circuit having blood and non-blood portions, a controller waste, dialysate, and treatment fluid pumps connected to a hemodiafilter, a pressure sensor at an inlet of the waste pump, and flow controllers permitting selective interconnection of the blood and non-blood portions. The controller controls a net ultrafiltration, during a treatment mode, by independently regulating the speed of the waste pump that draws fluid from a hemodiafilter, the speed of a replacement fluid pump that pumps replacement fluid into the blood portion, and the speed of the dialysate pump that pumps dialysate into the hemodiafilter. The controller controls the pumps to implement first and second synchronization modes and a treatment mode. In the first synchronization mode, the controller detects a target pressure at an inlet of the waste pump while flowing blood through the hemodiafilter and while blocking flow through the replacement fluid and waste pumps. Subsequently, in the first synchronization mode, the controller pumps dialysate through the hemodiafilter using the dialysate and waste pumps and controlling the waste pump speed to establish a predetermined dialysate flow rate, controlling the dialysate pump speed to determine a synchronized dialysate pump speed that maintains the waste pump inlet pressure at said target pressure. Subsequently, in the second synchronization mode, the controller connects the replacement fluid pump and the waste pump directly in series and, while flowing replacement fluid between them and controlling the waste pump speed establish a predetermined hemofiltration rate, controlling the replacement fluid pump speed to determine a synchronized replacement fluid pump speed that maintains the waste pump inlet pressure at said target pressure. Subsequently, in a treatment mode, the controller connects the replacement fluid pump to pump replacement fluid into the blood portion at said synchronized replacement fluid pump speed, connect said dialysate pump to pump dialysate into said hemodiafilter at said synchronized dialysate pump speed, and to connect said waste pump to draw waste fluid from the hemodiafilter at a rate responsive to the predetermined dialysate flow rate and the predetermined hemofiltration rate.

In variations thereof, the third embodiments include ones in which in the treatment mode, the waste pump is controlled to draw waste fluid from the hemodiafilter at a rate equal to the sum of the predetermined dialysate flow rate and the predetermined hemofiltration rate.

According to fourth embodiments, the disclosed subject matter includes a method for controlling flow in a fluid circuit. The method includes, in a treatment machine that controls the total volume of fluid flowing into or from a patient against the total volume of fluid drawn from the patient by regulating the relative speeds of peristaltic pumps that flow fluid in a fluid circuit connected to the patient, implementing a priming mode in which priming fluid is pumped through the fluid circuit the priming mode including pumping fluid through the fluid pumps for a break-in interval of at least five minutes, before establishing a treatment mode in which the peristaltic pumps are used to control a net flow of fluid into or from the patient.

In variations thereof, the fourth embodiments include ones in which the treatment machine is a hemodialysis machine and the pumps regulate the flow of dialysate into and out of a dialyzer. In variations thereof, the fourth embodiments include ones that include after said break-in interval, performing a flow calibration procedure in which the flow of one of said peristaltic pumps is calibrated against a standard or another of said peristaltic pumps. In variations thereof, the fourth embodiments include ones in which the calibration procedure generates a control parameter that is used by the controller to regulate said peristaltic pumps during the treatment mode.

Figure 12:
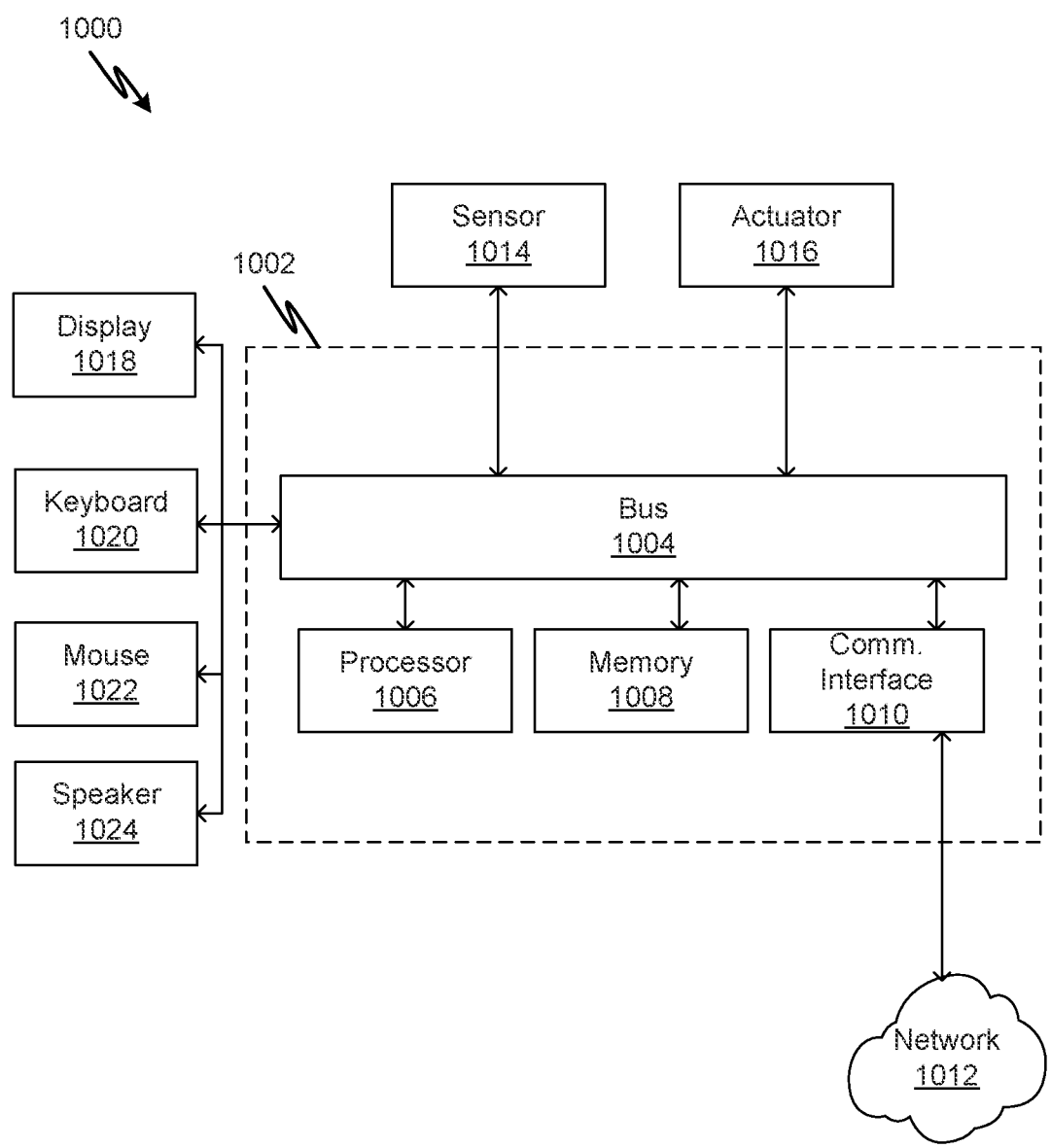
FIG. 12 shows a computer system which may form a basis for control system and other programmable devices described herein.

FIG. 12 shows a block diagram of an example computer system according to embodiments of the disclosed subject matter. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C #, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

It will be appreciated that the modules, processes, systems, and sections described above can be implemented in hardware, hardware programmed by software, software instruction stored on a non-transitory computer readable medium or a combination of the above. For example, a method for controlling balancing in renal replacement therapy, for synchronizing balanced pumps, etc. can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C #.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control engineering, medical systems, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, synchronization devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A method of controlling pumps, that include an inlet peristaltic pump and an outlet peristaltic pump, in a hemofiltration system, comprising:
    connecting the inlet peristaltic pump, by a connecting channel, in series with the outlet peristaltic pump;
    pumping with the inlet peristaltic pump and the outlet peristaltic pump while measuring a pressure within the connecting channel between the inlet peristaltic pump and the outlet peristaltic pump until the measured pressure stabilizes within a predefined time interval;
    varying an inlet peristaltic pump speed until the inlet peristaltic pump speed reaches a first value at which the pressure reaches a predefined target pressure P1;
    increasing only the inlet peristaltic pump speed to a second value greater than the first value and recording a pressure P2 within the connecting channel corresponding to the second value of the inlet peristaltic pump speed;
    after the increasing, decreasing only the inlet peristaltic pump speed to a third value smaller than the first value and recording a pressure P3 within the connecting channel corresponding to the third value of the inlet peristaltic pump speed;
    fitting a line to at least points defined by the predefined target pressure P1 and the first value of the inlet peristaltic pump speed, pressure P2 and the second value of the inlet peristaltic pump speed, and pressure P3 and the third value of the inlet peristaltic pump speed;
    deriving a parameter $I_{comp}$ from a slope of the fitted line; and
    using the parameter $I_{comp}$ to control the inlet peristaltic pump speed.

2. The method of claim 1, wherein the inlet peristaltic pump is configured to pump replacement fluid into a blood line.

3. The method of claim 1, wherein the outlet peristaltic pump is configured to withdraw waste fluid from a hemofilter.

4. The method of claim 3, wherein the predefined target pressure is obtained by measuring the pressure in a waste compartment when there is no flow across a membrane of the hemofilter and while blood is flowing such that a predefined average pressure exists on a blood side of the hemofilter.

5. The method of claim 4, wherein the predefined average pressure on the blood side is measured at a selected blood pumping speed.

6. A system for controlling flow in a fluid circuit, comprising:
    a hemofiltration machine with fluid circuit having blood and non-blood portions, a controller, a waste pump, a dialysate pump, and a treatment fluid pump connected to a hemodiafilter, a pressure sensor at an inlet of the waste pump, and flow controllers permitting selective interconnection of the blood and non-blood portions;
    the controller controlling a net ultrafiltration, during a treatment mode, by independently regulating a speed of the waste pump that draws fluid from the hemodiafilter, a speed of a replacement fluid pump that pumps replacement fluid into the blood portion, and a speed of the dialysate pump that pumps dialysate into the hemodiafilter;
    the controller controlling the pumps to implement first and second synchronization modes and the treatment mode;
    in the first synchronization mode, the controller detecting a target pressure at an inlet of the waste pump while flowing blood through the hemodiafilter and while blocking flow through the replacement fluid and waste pumps;
    subsequently, in the first synchronization mode, the controller controlling pumping of dialysate through the hemodiafilter using the dialysate pump and the waste pump and controlling the waste pump speed to establish a predetermined dialysate flow rate, controlling the dialysate pump speed to determine a synchronized dialysate pump speed that maintains the waste pump inlet pressure at said target pressure;
    subsequently, in the second synchronization mode, the controller connecting the replacement fluid pump and the waste pump directly in series and, while flowing replacement fluid between them and controlling the waste pump speed to a first value that establishes a predetermined hemofiltration rate, controlling the replacement fluid pump speed to determine a synchronized replacement fluid pump speed that maintains the waste pump inlet pressure at said target pressure, and perturbing only the replacement fluid pump speed to a higher speed than the first value and to a lower speed than the first value and calculating a calibration parameter based on pressures measured at the higher speed and at the lower speed;

subsequently, in the treatment mode, the controller connecting the replacement fluid pump to pump replacement fluid into the blood portion at said synchronized replacement fluid pump speed, connect said dialysate pump to pump dialysate into said hemodiafilter at said synchronized dialysate pump speed, and to connect said waste pump to draw waste fluid from the hemodiafilter at a rate responsive to the predetermined dialysate flow rate and the predetermined hemofiltration rate.

7. The system of claim 6, wherein, in the treatment mode, the waste pump is controlled to draw the waste fluid from the hemodiafilter at a rate equal to a sum of the predetermined dialysate flow rate and the predetermined hemofiltration rate.

\* \* \* \* \*